US008546115B2

(12) United States Patent
Buchert et al.

(10) Patent No.: US 8,546,115 B2
(45) Date of Patent: Oct. 1, 2013

(54) ESTERASES AND THEIR USE

(75) Inventors: Johanna Buchert, Espoo (FI); Tiina Nakari-Setälä, Espoo (FI); Pasi Halonen, Turku (FI); Hanna Kontkanen, Vantaa (FI); Ann Westerholm-Parvinen, Kirkkonummi (FI); Marjaana Rättö, Vantaa (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 545 days.

(21) Appl. No.: 12/668,313

(22) PCT Filed: Jul. 8, 2008

(86) PCT No.: PCT/FI2008/050419
§ 371 (c)(1),
(2), (4) Date: Mar. 30, 2010

(87) PCT Pub. No.: WO2009/007510
PCT Pub. Date: Jan. 15, 2009

(65) Prior Publication Data
US 2010/0209985 A1    Aug. 19, 2010

(30) Foreign Application Priority Data
Jul. 10, 2007   (FI) ..................................... 20075532

(51) Int. Cl.
*C12N 9/18*    (2006.01)
(52) U.S. Cl.
USPC ................... 435/136; 435/320.1; 435/254.11; 435/267; 435/197; 435/198
(58) Field of Classification Search
None
See application file for complete search history.

(56) References Cited

U.S. PATENT DOCUMENTS

| | | | |
|---|---|---|---|
| 5,990,069 | A | 11/1999 | Andre et al. |
| 6,255,451 | B1 | 7/2001 | Koch et al. |
| 2002/0123123 | A1 | 9/2002 | Svendsen et al. |
| 2004/0031072 | A1 | 2/2004 | La Rosa et al. |
| 2007/0134779 | A1 | 6/2007 | Dyson et al. |

FOREIGN PATENT DOCUMENTS

| WO | WO 2004-029193 | 4/2004 |
|---|---|---|
| WO | WO-2007/093677 A1 | 8/2007 |

OTHER PUBLICATIONS

Seffernick et al. (J. Bacteriology, vol. 183, pp. 2405-2410, 2001).*
Wells, Biochemistry, vol. 29, pp. 8509-8517, 1990.*
Wang et al. (Fungal Genetics 2002, vol. 35 (3), pp. 261-276).*
Tsang et al. (Direct Submission, Accession No. DY850366, Mar. 24, 2006).*
Bernfeld, "Amylases, α and β", In: Colowick and Kaplan (eds.), Methods of Enzymology, vol. 1, 1955, Academic Press, pp. 149-158.
Carvalho et al., "Cutinase: From Molecular Level to Bioprocess Development", Biotechnol Bioeng, vol. 66, No. 1, 1999, pp. 17-34.
Coen, "Quantitation of Rare DNAs by PCR", In: Ausubel, Brent, Kingston, More, Seidman, Smith, and Struhl (eds.), Current Protocols in Molecular Biology, John Wiley & Sons, 2001, pp. 15.7.1-15.7.8.
Database DGENE, ADK70253 protein, *Aspergillus* sp., ester hydrolase protein, 2004.
Database UniProtKB, A4RFE1_MAGGR, Acession No. A4RFE1, hypothetical protein, ORF Name: MGG_00376, Magnaporthe grisea, entry ver. 4, 2007. Database UniProtKB, CUTI_BOTCI, Accession No. Q00298, cutinase precursor, Botrytis cinerea, entry ver. 39, 2007.
Database UniProtKB, A4RFE1_MAGGR, Acession No. A4RFE1, hypothetical protein, ORF Name: MGG_00376, Magnaporthe grisea, entry ver. 4, 2007.
Database UniProtKB, CUTI_BOTCI, Accession No. Q00298, cutinase precursor, Botrytis cinerea, entry ver. 39, 2007.
Davies et al., "Evidence for a role of cutinase in pathogenicity of Pyrenopeziza brassicae on brassicas", Physiological and Molecular Plant Pathology, 2000, vol. 57, pp. 63-75.
EMBL Nucleotide Sequence Database, Accession No. DY849925, pBluescript C. cinerea cDNA clone CcinSEQ17107, mRNA sequence, ver. 2, 2006.
EMBL Nucleotide Sequence Database, Accession No. EE296673, EST 0471 Mycelia Grown in Crab Chitin, Hypocrea virens cDNA clone TvC104G04, mRNA sequence, ver. 2, 2006.
Fett et al., "Cutinase Production by *Streptomyces* spp.", Current Microbiology, 1992, vol. 25, No. 3, pp. 165-171.
Garcia-Lepe et al., "Lipases in autolysed cultures of filamentous fungi", Letters in Applied Microbiology, 1997, vol. 25, pp. 127-130.
Gindro et al., "Purification and characterization of a 40.8-kDa cutinase in ungerminated conidia of *Botrytis cinerea* Pers.: Fr.", FEMS Microbiology Letters, 1999, vol. 171, pp. 239-243.
Kolattukudy, "Cutinases from fungi and pollen", In: Borgström and Brockman (eds.), Lipases, Elsevier, 1984, pp. 471-504.
Köller et al., "Purification and Characterization of Cutinase from *Venturia inaequalis*", Phytopathology, 1989, vol. 79, No. 3, pp. 278-283.
Köller et al., "Role of cutinase and cell wall degrading enzymes in infection of Pisum sativum by *Fusarium solani* f. sp. pisi", Physiological Plant Pathology, 1982, vol. 20, pp. 47-60.
Kontkanen et al., "Characterisation of steryl esterase activities in commercial lipase preparations", Journal of Biotechnology, 2004, vol. 108, pp. 51-59.
Lee et al., "Agrobacterium T-DNA-mediated integration and gene replacement in the brown rot pathogen *Monilinia fructicola*", Curr Genet, 2006, vol. 49, No. 5, pp. 309-322.

(Continued)

*Primary Examiner* — Hope Robinson
(74) *Attorney, Agent, or Firm* — Birch, Stewart, Kolasch & Birch, LLP

(57) ABSTRACT

The present invention relates to polyesterases having cutinase and/or suberinase activity obtainable from *Coprinus* and *Trichoderma*. The invention further relates to a method for producing the polyesterases, and to polynucleotides, vectors and host cells used therein. The enzymes are useful in hydrolysing cutin, suberin and other polyesters for example in treating agricultural or food raw materials, or wood raw materials, pulp and paper products and waste, and in modifying polyester fibers, or in laundry and dish applications.

8 Claims, 2 Drawing Sheets

(56) References Cited

OTHER PUBLICATIONS

Machida et al., "Genome sequencing and analysis of *Aspergillus oryzae*", Nature, 2005, vol. 438, pp. 1157-1161, GenBank Accession No. BAE58548.

Maeda et al. "Purification and characterization of a biodegradable plastic-degrading enzyme from *Aspergillus oryzae*", Appl Microbiol Biotechnol, 2005, vol. 67, pp. 778-788.

Margolles-Clark et al., "Cloning of Genes Encoding • -L-Arabinofuranosidase and • -Xylosidase from *Trichoderma reesei* by Expression in *Saccharomyces cerevisiae*", Applied and Environmental Microbiology, 1996, vol. 62, No. 10, pp. 3840-3846.

Pentilla et al., "A versatile transformation system for the cellulolytic filamentous fungus *Trichoderma reesei*", Gene, 1987, vol. 61, pp. 155-164.

Raeder et al., "Rapid preparation of DNA from *Filamentous fungi*", Letters in Applied Microbiology, 1985, vol. 1, pp. 17-20.

Tenkanen et al., "Hydrolysis of steryl esters by a lipase (Lip 3) from *Candida rugosa*", Appl Microbiol Biotechnol, 2002, vol. 60, pp. 120-127.

Thompson et al., "CLUSTAL W: improving the sensitivity of progressive multiple sequence alignment through sequence weighting, position-specific gap penalties and weight matrix choice", Nucleic Acids Research, 1994, vol. 22, No. 22, pp. 4673-4680.

Trail et al., "Diversity of cutinases from plant pathogenic fungi: Purification and characterization of two cutinases from *Alternaria brassicicola*", Physiological and Molecular Plant Pathology, 1993, vol. 42, pp. 205-220.

van der Vlugt-Bergmans et al., "Cloning and Expression of the Cutinase A Gene of *Botrytis cinerea*", Molecular Plant-Microbe Interactions, 1997, vol. 10, No. 1, pp. 21-29.

Wei et al., "A Novel Variant of the Catalytic Triad in the Strepotomyces Scabies Esterase", Nature Structural Biology, vol. 2, No. 3, 1995, pp. 218-223, XP002589868.

European Search Report issued Aug. 4, 2010, in EP 08787696.7.

\* cited by examiner

Figure 1

```
CC1G_09668    MKFTTLATLALGAVSALAAPVTE---------------LESKQLFCKDVYVFFAPGTGEV  45
CC1G_03922    MKFTTLNTLALGAVSALAAPAAE---------------LESPQLFCPDVYVFFARGTGEI  45
CC1G_11503    MKFFALATLAIGALSALAAPVAQ---------------IDTRQLRCDDVYVFFARGTTEI  45
CC1G_07482    MKFSALVALALG§ATFAAPIG-----------------LEARQGTCSDVYVFFVPGTTET  44
CC1G_09365    MRLSPLLPLITLASLTLATPVPIPNPIIEHDDLDIRDLLEAPQVTCRSVHVLFARGTAET  60
CC1G_05430    MVSKSLTSLVLLAFTLTGVAAAP---------------APTTPCAQVHIIAAKASTEP   43
                 .   *   *     ...           :          *  ::: .*.: *

CC1G_09668    GT-LGTVVGPGLSAAVKLAVPD--SVEFEGIDYPALVSGYLAGGDRGGAKTMANKVSQTA 102
CC1G_03922    GT-LGTVVGPSFSAAVSLAVRG--SVDFEGIDYPALVTGYLAGGDPGGARTMADKVASTA 102
CC1G_11503    GT-LGTVIGPPLRTAVSRAVRG--SVTFEGIDYPAVVAGFLAGGDRGGARTMAQKVSSIA 102
CC1G_07482    PAPLGDRIAPFFADALVKLVPEK-SVEFTGVPYAAGLIGYLIGGDPEGAKTMANMVTTTV 103
CC1G_09365    PT-LGEVVGPGFPDNLIRVLPSGPTLCFAGISYAASYLGYLQGGDREGAKTMATAAAHIA 119
CC1G_05430    PG--PGIVGQLITQIQNQSSQT---VSTDSVDYPATLENYHESSS-AGTAALKTHLTNQA  97
                 :  :             :      :  * .  .:  ...   ^: ::    :  .

Serine active site
CC1G_09668    SRCPNAKIFISGYSQGAQVT-----------HLAAPQLSAADQAKVTGVVTFGDP---- 146
CC1G_03922    SRCPNAKIFISGYSQGAQVT-----------HLAARQLSAANQAPVTGVVTFGDP---- 146
CC1G_11503    AQCPDAKIFISGYSQGAQVT-----------HLAAKQLSAADQAPVTGVITFGDP---- 146
CC1G_07482    PQCSNAKIFMSGYSQGAQVT-----------HLAAPQLSDEDLDKVTGVVTFGDP---- 147
CC1G_09365    KSCPSAKIFLSGYSQGAQVV-----------HLAAQLASSVQSPINGVITFGDP---- 163
CC1G_05430    NPCPNQKIVLIGYSQGAHIIGDTLAGGGGGLLGTPTPAIDCSIAHPVVAVAAFGDPAHV§ 157
               . **.::.: ***** ::              :   :      .:  .*  **.*

Aspartate and Histidine active site
CC1G_09668    ---------YPDDALPG--------GLQSRKKTY NVGDLI LPTLLAP FTYGSDTP 189
CC1G_03922    ---------YPDDALPG--------GLDSRPITY FCDLI DSLPTLLAP LTYGSDAS 189
CC1G_11503    ---------NKDPALPG--------GLENPRKTF AGDLI APSTILLP LTYGSDAT 189
CC1G_07482    ---------YPDTALPG--------TLEQRKKTF KNGDLI EPVHLPLPA FEYRNDAE 190
CC1G_09365    ---------TVKKALPG--------AMENKPITE DCDKI EGLPLVTDP WNYKSSWD 206
CC1G_05430    GKSYNEGTARRDGMPPRGLTQDYSLTFKSPVASH DFNDLF SASGLST-IV LTYLERYQN 217
                    .:         :     . .*::::  .*  ::        *   *  *

CC1G_09668    DAAPWIAAPV-- 199
CC1G_03922    DAARWVAARV-- 199
CC1G_11503    EAASFIAGKV-- 199
CC1G_07482    EAAPWVADPY-- 200
CC1G_09365    PAARWJAFPV-- 216
CC1G_05430    DAARFVLDKIGG 229
              ^* :: ::
```

ESTERASES AND THEIR USE

FIELD OF THE INVENTION

The present invention relates to novel esterases, and more precisely to polyesterase proteins having cutinase and/or suberinase activity. Said enzymes may be obtained from the fungal genus *Coprinus* or *Trichoderma*. The invention also relates to isolated polynucleotides encoding said proteins, and to vectors and genetically modified microorganisms comprising the polynucleotides, as well as to a method for producing the proteins. Still further the invention relates to an enzyme preparation comprising the polyesterase protein, and to the use of the protein or preparation. Finally the invention relates to a method of hydrolysis of cutin and/or suberin or other polyesters using the polyesterases.

TECHNICAL BACKGROUND

Cutinases and suberinases are polyesterases, which are able to degrade or partially depolymerise plant polyester waxes, i.e. cutin and suberin. Significant amounts of cutin/suberin are present in different agricultural and forest raw materials and by-products, such as birch bark and cork, berries, cereals, vegetables and their processing by-products. The presence of these waxes in plant raw materials may impair the industrial processing of plant materials due to their hydrophobic character and recalcitrant structure.

Modification of the polyesters would improve the processing and exploitation of several natural materials, and would reduce disposal of process co-products or wastes. These waste fractions could be exploited as a source of more valuable compounds, e.g. suberin-based oligoesters could be potential raw materials in lubricants and binders. The use of polyesterases improve the processing and exploitation of several plant materials, such as cereals, fruits, vegetables and berries, and also improve release and recovery of valuable bioactive and functional components from these raw materials.

Sustainable use of natural resources and waste management contribute to minimise waste production. The use of enzymes in synergy with chemical and physical processes is an environmentally friendly means to add value to waste co-products. Cutinases/suberinases can also be utilised e.g. in laundry and dishwashing applications to remove fats as well as in cotton bio-scouring and surface modification of man-made polyester fibres.

Although lipids and waxes are abundant constituents of different industrial products and lignocellulosic residues, only a limited set of lipid modifying enzymes, other than conventional lipases, are commercially available. Cutinases and suberinases are regarded as potential enzymes for modification of natural lipids and waxes, which cannot be hydrolyzed by conventional lipases.

A cutinase from the plant/human pathogen fungus *Fusarium solani* sp. *pisi* is the most studied cutinase so far (Carvalho et al., 1999), but cutinases have also been found in microorganisms such as *Alternaria brassicicola* (Trail and Köller, 1993), *Botrytis cinerea* (Gindro and Pezet 1999), *Venturia inaequalis* (Köller and Parker, 1989), *Aspergillus oryzae* (Maeda et al., 2005) and in certain *Streptomyces* species (Fett et al., 1992). All of the biochemically well-characterized cutinases are serine esterases, containing the classical Ser-His-Asp triad common in serine proteases and in several lipases. The characterized cutinases possess a pH optimum from neutral to alkaline.

Cutinases have been suggested for a number of uses of which only a few are mentioned herein. WO2004/029193 for example suggests the use of lipases including cutinases in fermentation processes, in particular in ethanol production processes. U.S. Pat. No. 6,255,451 relates to degradation of biodegradable polymers with lipase and cutinase. A great number of potential lipolytic enzyme production organisms have been listed, including i.a. *Coprinus cinerius* and *Trichoderma reesei*. However, there is no disclosure of lipases from these organisms. Garcia-Lepe et al., 1997 screened for lipase activity in autolysed cultures of fifty-one fungi from different genera and strains. Fungi from the genus *Fusarium* were found to be the best producers of lipase activity and they also showed a low activity on cutin and suberin. *Aspergillus* was also found to have some activity, whereas *Penicillium* species had very low activity. Other species and strains from genus *Trichoderma*, order Mucorales and class Basidiomycetes did not show lipase activity.

Cutinases are frequently produced by phytopathogenic fungi, because they are involved in the disruption of structural cutin polymer of higher plants. Cutinases are secreted proteins, which allow pathogenic fungi to penetrate through the cuticular barrier into the host plant during the initial stage of fungal infection. However, phytopathogenic fungi are undesirable sources of industrial enzymes due to negative user perceptions. In fact, food grade poly-esterases and suberin-processing enzymes are currently not commercially available. Thus there is still a need for novel and more efficient polyesterases. The present invention meets this need.

SUMMARY OF THE INVENTION

One object of the present invention is a polyesterase protein comprising an amino acid sequence having at least 50% sequence identity to SEQ ID NO: 2, 6, 11, or 13, or a variant or fragment thereof having polyesterase activity.

Another object of the invention is an isolated polynucleotide selected from the group consisting of
a) a polynucleotide comprising a nucleotide sequence of SEQ ID NO: 1, 3, 5, 10 or 12, or a nucleotide sequence encoding a protein of claim 1,
b) a complementary strand of a), and
c) a sequence that is degenerate as a result of the genetic code to any one of a) or b).

One further object of the invention is a vector comprising said polynucleotide, and a genetically modified microorganism, which has been transformed with this vector.

Still one object of the invention is a method for producing said poly-esterase protein, which method comprises transforming a microorganism with a vector comprising said polynucleotide, culturing the transformed microorganism under conditions allowing the expression of said polynucleotide, and recovering the expressed protein.

The invention also encompasses an enzyme preparation comprising said polyesterase protein.

Further the invention encompasses a method of hydrolysis of cutin, suberin, or other polyester, said method comprising treating a cutin, suberin, or other polyester containing material with said polyesterase protein under conditions allowing partial or total hydrolysis of said polyester.

Still further the invention encompasses the use of said polyesterase protein or enzyme preparation in food industry, pulp and paper industry, textile industry, or in laundry and dishwashing applications, or in chemical synthesis. Specific embodiments of the invention are set forth in the dependent claims. Other objects, details and advantages of the present invention will become apparent from the following drawings, detailed description and examples.

BRIEF DESCRIPTION OF THE DRAWINGS

FIG. 1 shows the amino acid sequences of the cutinase-like proteins of *Coprinus cinereus*. CC1G_09688 corresponds to SEQ ID NO: 2, CC1G_03922 corresponds to SEQ ID NO: 7, CC1G_11503 corresponds to SEQ ID NO: 8, CC1G_07482 corresponds to SEQ ID NO: 4, CC1G_09365 corresponds to SEQ ID NO: 9, and CC1G_05430 corresponds to SEQ ID NO: 6.

DETAILED DESCRIPTION OF THE INVENTION

Figure 2:
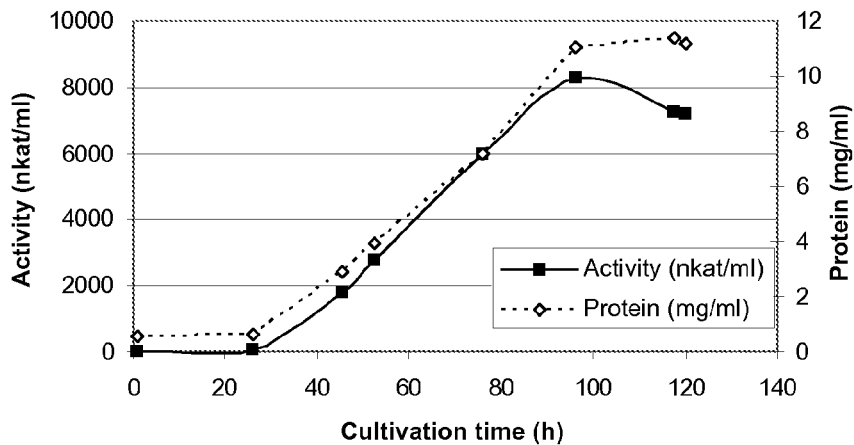
FIG. 2 shows extracellular production of *Coprinus cinereus* cutinase 09668 (CcCUT) in a 20 L bioreactor cultivation.

The invention provides novel enzyme proteins, which are capable of hydrolysing ester bonds in natural and man-made polyesters. At least some of them have substantial activity also at acidic pH, which is an advantage in certain applications. The proteins are "esterases", which encompass enzymes classified in (EC 3.1.1), also called carboxylic ester hydrolases. In particular the proteins of the present invention are "polyesterases", which means that they have significant activity on various polyesters, such as e.g. plant polyester waxes, i.e. cutin and suberin or man-made polyesters. According to a preferred embodiment of the invention the protein has cutinase activity. "Cutinase" is an enzyme classified in (EC 3.1.1.74). A cutinase is a serine esterase containing the classical Ser, His, Asp triad of serine hydrolases. According to another embodiment of the invention the protein has suberinase activity. "Suberinase" is an enzyme capable of degrading suberin. The proteins may have more than one of said enzyme activities as measured by using model substrates or isolated cutin or suberin as substrate. The polymerase activity may thus be at least cutinase activity, or suberinase activity, or both. In addition the proteins may have other enzyme activities such as e.g. lipase activity, which is also classified in EC 3.1.1.

The polyesterases comprise an amino acid sequence that has at least 50%, or preferably at least 60%, 70%, 80%, 90%, 95% or 98% sequence identity to SEQ ID NO: 2, 6, 11 or 13, or a variant, or fragment thereof having polyesterase activity. According to a preferred embodiment, the polyesterase comprises an amino acid sequence having at least 50% sequence identity to SEQ ID NO:2, or a variant or fragment thereof having cutinase activity. Such polyesters are e.g. those comprising the amino acid sequence of SEQ ID NO: 4, 7, 8 or 9, or an enzymatically active variant or fragment thereof. Such a protein may have at least 50, 60, 70, 80, 90, 95 or 98% sequence identity to SEQ ID NO: 4.

The term "identity" means here the sequence identity between two amino acid sequences compared to each other. The identity of sequences is here determined using Clustal w multiple alignment programme found on the webpages of European Molecular Biology Laboratory-European Bioinformatics Institute (EMBL-EBI; www.ebi.ac.uk/clustalw/) using default settings and Blosum62 as substitution matrix (Thompson et al., 1994).

It is well known that deletion, addition or substitution of one or a few amino acids does not necessarily change the catalytic properties of an enzyme protein. Therefore the invention also encompasses variants and fragments of the given amino acid sequences having polyesterase activity. The term "variant" as used herein refers to a sequence having minor changes in the amino acid sequence as compared to a given sequence. Such a variant may occur naturally e.g. as an allelic variant within the same strain, species or genus, or it may be generated by mutagenesis or other gene modification. It may comprise amino acid substitutions, deletions or insertions, but it still functions in substantially the same manner as the given enzymes, in particular it retains its catalytic function as a polyesterase.

A "fragment" of a given protein sequence means part of that sequence, i.e. a sequence that has been truncated at the N- and/or C-terminal end. It may for example be the mature part of a protein comprising a signal sequence, or it may be only an enzymatically active fragment of the mature protein.

The invention is also directed to isolated polynucleotides, which encode the polyesterases disclosed, including complementary strands and degenerate strands. A polynucleotide that is "degenerate as a result of the genetic code" to a given sequence, means that it contains one or more different codons, but encodes for the same amino acids. A "polynucleotide" as used herein may be a single or double stranded polynucleic acid. The term encompasses genome DNA, cDNA and RNA.

Genes from different organisms encoding enzymes with the same catalytic activity often have sequence similarities. These similarities can be exploited in many ways to clone other genes from other organisms with the same or similar catalytic activity.

Polynucleotides encoding the novel esterases may be identified e.g. in silico by comparing nucleotide sequences. If such sequences are not available one can identify a conserved region in the nucleotide or amino acid sequence and clone a gene fragment using PCR techniques. Cloning means transfer of a DNA fragment of interest from one organism to a self-replicating genetic element and furthermore, possibly to a foreign host cell. After sequencing the fragment the complete gene can be obtained e.g. by using a cDNA library in a manner known per se. Another way to identify a polyesterase gene is by conventional nucleic acid hybridization.

Specific probes for cloning can be prepared for example from corresponding mRNA or the probe can be prepared if part of the amino acid sequence of the protein encoded by the gene is known. Once candidate DNA sequences have been determined, algorithmic methods can be utilized to efficiently search a target genome for matches. BLAST (Basic Local Alignment Search Tool) is a widely used system designed for this purpose.

The proteins or polynucleotides of the invention may be derived from any suitable organism including bacterial, fungal, yeast, plant or mammalian cells containing them. Preferably the enzyme is derived from a fungus, and in particular from a filamentous fungus e.g. from the genus *Coprinus* or *Trichoderma*, and especially from *C. cinereus*, or *T. reesei* (*Hypocrea jecorina*).

Proteins or polynucleotides "derived from" a particular organism encompass products isolated from said organism, as well as modifications thereof. A protein derived from a particular organism may be a recombinantly produced product, which is identical to, or a modification of the naturally occurring protein. The protein may also be modified e.g. by glycosylation, phosphorylation or other chemical modification. The modification may also include attachment of a suitable peptide or protein fusion partner to the protein of interest. The fusion partner may have a beneficial role, such as it may enhance the hydrolysis or processing efficiency of the protein of interest, or the fusion partner may aid in purification of the protein of interest. Examples of such fusion partners are e.g. fungal hydrophobins. Products derived from the particular organism also encompass mutants and natural variants of the products, where one or more nucleic acid and/or amino acid is deleted, inserted and/or substituted.

As set forth above, the protein may be isolated from the organism, where it occurs naturally, or it may be produced recombinantly in a host cell, or produced synthetically e.g. by peptide synthesis. Preferably the protein is a recombinant protein. It may be prepared by first isolating a fragment comprising the protein encoding polynucleotide by amplification in a PCR reaction (Coen, 2001) or other recombinant DNA methods (Sambrook et al., 1989). The isolated polynucleotide is then inserted into a vector e.g. a plasmid vector, especially an expression vector, which comprises the following operably linked elements: a transcriptional promotor, a segment encoding the polyesterase, and a transcriptional terminator. The promotor is preferably a strong promotor, which enables overexpression of the protein. One suitable promotor is the cellobiohydrolase I (cbh1) promotor of *T. reesei*. The promoter is chosen to be capable of driving expression of the gene of interest in the selected production host. The vector can be one that is integrated into the chromosome or an autonomously replicating one.

The vector is then transformed into a heterologous or homologous host cell to generate a "genetically modified microorganism", which is cultivated under conditions enabling the expression of the protein. Methods for protein production by recombinant technology in different host systems are well known in the art (Gellissen, 2005). Alternatively only the strong promotor is operably linked to the polyesterase gene on the host's chromosome, whereby the expression of said gene is overexpressed. The host cell may be any suitable eukaryotic or prokaryotic cell. Preferably it is a fungus e.g. a filamentous fungus or yeast, and most preferably it belongs to the genus *Trichoderma*, especially it is *T. reesei*. It may also be a *Saccharomyces* or a *Pichia* strain, such as *S. cerevisiae* and *P. stipitis*, respectively. Further it may be an *Aspergillus* strain, such as *A. nidulans, A. niger* or *A. oryzae* or even a bacterial host.

The polyesterase protein is preferably produced extracellularly, whereby the secreted protein may be obtained from the culture medium. Alternatively the cells may be disrupted to release the enzyme, which then may be obtained from the supernatant after removal of the cell debris. The enzyme may be further purified using various protein purification methods, if desired. Such purification may include e.g. concentration, precipitation, chromatography, immunopurification, phase separation etc. to remove other proteins and especially other enzymes.

An "enzyme preparation" in the present context may be any composition comprising at least one of the polyesterases of the invention. It may further comprise one or more other enzymes. It may be in crude form, e.g. in the form of a spent culture or cell supernatant, or it may contain the polyesterase in a purified or substantially purified form.

The polyesterases are useful for hydrolysis of cutin, suberin or other polyester containing material. The cutin and/ or suberin containing material is usually of plant origin, whereas the other polyester containing material may be plant-derived or man-made. An amount of the enzyme efficient to catalyze the desired reaction is added to the material to be treated under conditions allowing hydrolysis. The polyesterases may e.g. be used to degrade or partially depolymerise plant polyester waxes, i.e. cutin and suberin. The polyesterases may thus be used e.g. for treating agricultural or food raw materials or by-products obtained from vegetables, fruits, berries, and cereals. They may also be applied in non-food processes e.g. in methods comprising treating of wood raw materials, pulp and paper products, or process wastes or waters or by-products, or modifying synthetic or other man-made polyester fibres or textiles, or removing stickies or fat from laundry and dishes.

The polyesterases may under appropriate conditions also be used for catalyzing a reverse reaction i.e. esterification, that is formation of ester bonds e.g. between fatty acids and alcohols.

The invention is illustrated by the following non-limiting examples. It should be understood, however, that the embodiments given in the description above and in the examples are for illustrative purposes only, and that various changes and modifications are possible within the scope of the claims.

Example 1

Measurement of Polyesterase Activities

Methods to Model Suberin Degradation

The degradation of the aliphatic layer of suberin was imitated by model substrates, i.e. naphthol derivatives differing both in the bulkiness of the chromophore (1-naphthyl, 2-naphthyl, Naphthol AS, Naphthol AS-D) and the length of the ester-bonded carbon chain. Substrate solutions of naphthol derivatives (0.5-1 mM) were prepared in 1% acetone and 1% TRITON™ X-100 (non-ionic octylphenol ethoxylate surfactant) in 50 mM Na-citrate (pH 5) or 50 mM NaP (pH 8). The reaction mixture containing 170 µl substrate solution and 10 µl enzyme sample was incubated at 40° C. for 20 minutes. After incubation, 20 µl of 1% Fast Blue BB salt dye was added, and absorbance (1NA substrates—450 nm, 2NA substrates—510 nm, NAS substrates—595 nm, NASD substrates—595 nm) was measured after additional incubation of 10 min. The enzyme activities were determined by reference to a standard curve prepared from various amounts of 1NA, 2NA, NAS or NASD (the coloured reaction products).

The degradation of the layers of suberin containing aromatics was monitored with a model substrate 4-methylumbelliferyl 4-methyl ferulic acid ester (MUFE) containing p-coumaric acid derivatives (observed in native suberin) esterified with a fluorescent molecule (4-methylumbelliferone, 4MU). MUFE assay was performed by incubating 190 µl of 0.1 mM substrate solution with 10 µl of enzyme solution at 40° C. Fluorescence was measured ($\lambda_{ex}$=355 nm; $\lambda_{em}$=465 nm) after 20 min incubation using 4-methylumbelliferone (4MU) as standard.

Degradation of suberin was also measured using radioactively labelled suberin as a substrate. Suberin isolated from birch outer bark was labelled with [$^3$H]NaBH$_4$. The reaction mixture contained 10 mg suberin ($5 \times 10^5$-$10^6$ dpm/mg), 1.9 ml buffer (0.1% TRITON™ X-100 (non-ionic octylphenol ethoxylate surfactant) in 50 mM Na-citrate buffer, pH 5 or in 50 mM Na-phosphate buffer, pH 7) and 0.1 ml enzyme solution. The reaction mixture was incubated at 37° C., and reaction samples of 0.1 ml were taken during 48 h incubation. The hydrolysis products ($^3$H labelled monomers) released by the enzymatic action were extracted from reaction samples with ethyl acetate, and the resulting radioactivity was measured by liquid scintillation counter. The degree (%) of enzymatic degradation was quantified by measuring the radioactivity released after a total hydrolysis of suberin by alkali.

Methods to Model Cutin Degradation

Esterase activity modelling the cutinase activity was measured by a spectrophotometric assay (slightly modified from Davies et al., 2000) with 2.1 mM p-nitrophenyl butyrate (p-NPB) as substrate. The reaction was carried out in 0.1 M sodium phosphate buffer (pH 7.0) at 40° C. for 10 minutes and the amount of released p-nitrophenol was measured at 340 nm, using commercial p-nitrophenol as standard. This method enabled a convenient and rapid assay for non-specific esterase activity.

Cutinase activity was also measured using $^3$H labelled apple cutin as substrate by an adaptation of the methodology presented in Köller et al. (1982) and Davies et al. (2000). The reaction mixture contained 8 mg cutin ($5 \times 10^6$ dpm/mg), 1.9 ml master mix (containing 0.025% TRITON™ X-100 (nonionic octylphenol ethoxylate surfactant) in 50 mM Na-phosphate buffer, pH 7.0) and 0.1 ml enzyme solution. The reaction mixture was incubated at 37° C., and the reaction was followed for 24 h. The hydrolysis products ($^3$H labelled monomers) released by the action of cutinase were extracted from the reaction sample of 0.1 ml with ethyl acetate, and the resulting radioactivity was measured by liquid scintillation counter. The degree (%) of enzymatic degradation can be quantified by measuring the radioactivity released after a total hydrolysis of cutin by alkali.

Example 2

Screening of Polyesterolytic Activities

Altogether 55 microorganisms, mostly filamentous fungi, were screened for their ability to produce suberin modifying enzymes in suberin-induced conditions. The screening was based on the enzymatic assays of culture supernatants (hydrolysis of naphtol substrates and a fluorescently labelled aromatic compound and radiolabelled suberin, as described in Example 1) and GC/MS analysis of separated solids, whereby increased amounts of long fatty acids, such as hydroxy fatty acids and diols, confirmed that a microorganism was able to degrade suberin during its growth. *Coprinus cinereus* and *Trichoderma reesei* were found to be potential producers of cutin/suberin degrading enzymes.

Example 3

Genome Analysis of *Coprinus cinereus* for Polyesterase Encoding Genes

*Coprinus cinereus* was found to be able to produce polyesterases having activity on natural polyesters such as cutin and suberin (Example 2). The published genome of *Coprinus cinereus* (www.broad.mit.edu/annotation/genome/coprinus_cinereus/Home.html) was exploited for similarity searches based on known polyesterases (cutinases and suberinases), and six different cutinase-like genes were found. Protein similarities were analysed with Clustal w multiple alignment program. Five of the genes (CC1G_09668.1, CC1G_03922.1, CC1G_11503.1, CC1G_07482.1, and CC1G_09365.1) showed high sequence homology to cutinases and one (CC1G_05430.1) shared higher homology with acetyl xylan esterases (AXE) having e.g. a sequence identity of 30% with *Trichoderma reesei* AXE1. The results are shown in FIG. 1, where the serine active site and the aspartate and histidine active sites of the cutinases are indicated. Said genes and corresponding enzymes are hereinafter also simply called 09668, 03922, 11503, 07482, 09365 and 05430, respectively.

The sequence identities between the *Coprinus cinereus* cutinases analysed by Clustal w multiple alignment programme are shown in Table 1. Genes 09668, 03922, and 11503 had 199 amino acids, 07482 had 200 amino acids, 09365 had 216, and 05430 had 229 amino acids.

TABLE 1

Sequence identity between the *Coprinus cinereus* cutinases

| | 09668 | 03922 | 11503 | 07482 | 09365 | 05430 |
|---|---|---|---|---|---|---|
| 09668 | 100 | | | | | |
| 03922 | 88 | 100 | | | | |
| 11503 | 75 | 76 | 100 | | | |
| 07482 | 60 | 59 | 57 | 100 | | |
| 09365 | 53 | 53 | 49 | 53 | 100 | |
| 05430 | 29 | 30 | 25 | 25 | 24 | 100 |

Example 4

Genome Analysis of *Trichoderma reesei* for Polyesterase Encoding Genes

*Trichoderma reesei* was found to have activity against cutin and suberin (Example 2). The published genome of *T. reesei* (genome.jgi-psf.org/Trire2/Trire2.home.html) was exploited for similarity searches based on known cutinases, and one cutinase (like) gene (v1.2: tre17732, v2.0: tre60489, scaffold 7) was found.

A suberinase like gene (v1.2: tre40871, v2.0: tre31227, scaffold 37) was found through extensive blasting. Protein sequence of *Streptomyces scabies* suberinase was first used for blasting with BLAST program (blastp) at National Center for Biotechnology Information, NCBI using default parameters (Matrix: Blosum62, gap costs: existence 11, extension 1). Subsequently, *Trichoderma reesei* genome was blasted with fungal sequences having similarity with *S. scabies* suberinase (containing SEST-like domains) using default parameters.

Enzymes containing this SEST-domain act as esterases and lipases, but have little sequence homology to true lipases. The tertiary fold of these enzymes is substantially different from that of the alpha/beta hydrolase family and unique among all known hydrolases. Proteins containing this type of esterase domain have been found in a variety of hydrolases. Those with structural information include an esterase from *Streptomyces scabies* (SEST), a causal agent of the potato scab disease, which hydrolyzes a specific ester bond in suberin. Some hypothetical or putative proteins have also been found to have similarity with *S. scabies* esterase.

Example 5

Cloning of Novel Polyesterases from *Coprinus cinereus*

Three different types of polyesterases from Example 3 (09668, 07482, 05430) sharing lowest homology among themselves were selected for over-expression in *Trichoderma reesei*. The selected cutinases had optimal codon usage and suitable native signal sequences for the expression host.

For isolation of chromosomal DNA the *Coprinus cinereus* strain VTT-D-041011 was grown as mycelium in liquid cultures started from spores. The spores were inoculated in 50 ml of YP medium and grown for 2 days at 24° C. shaking. The mycelia were harvested by filtration and the genomic DNA was isolated by the method of Raeder and Broda, 1985. The genomic DNA was used as a template for PCR amplifications of the two cutinase genes (CC1G_09668.1, CC1G_07482.1) and the AXE-like gene (CC1G_05430.1) with primers which were designed to create a C-terminal $His_6$-tag and bearing phage lambda-based site specific recombination sequences. The native signal sequences of the genes were used. The primers used were the following; CC1G_09668.1 forward: SEQ ID NO: 14, CC1G_09668.1 reverse: SEQ ID NO: 15, CC1G_07482.1 forward: SEQ ID NO: 16, CC1G_07482.1 reverse: SEQ ID NO: 17, CC1G_05430.1 forward: SEQ ID NO: 18, CC1G_05430.1 reverse: SEQ ID NO: 19. The PCR reactions were done with the Phusion thermostable polymerase (Finnzymes, Finland) in a reaction mixture recommended by the manufacturer. The PCR program had an initial denaturation step of 30 seconds at 98° C., followed by 25 cycles of 10 seconds at 98° C., 30 seconds at 64° C. and 30 seconds at 72° C., where the annealing temperature was decreased with 1° C. per cycle until 50° C. was reached. This was followed by a final elongation step of 10 minutes at 72° C. The amplified PCR products were recombined into the Gateway donor vector pDONR221 (Invitrogen) by Gateway Recombination kit (Invitrogen) and sequenced. The sequences were as shown in Table 2.

TABLE 2

Cloned *Coprinus cinereus* cutinase sequences

| Gene | Cloned nucleotide sequence | Deduced amino acid sequence |
|---|---|---|
| C. cinereus 09668 clone 3.1 | SEQ ID NO: 1 | SEQ ID NO: 2 |
| C. cinereus 07482 clone 4.2 | SEQ ID NO: 3 | SEQ ID NO: 4 |
| C. cinereus 05430 clone 5.1 | SEQ ID NO: 5 | SEQ ID NO: 6 |

Two clones 3.1 and 3.5 of 09668 were sequenced. There were a few differences between the nucleotide sequences of clone 3.5 and the genome sequence, but all three nucleotide sequences encode the same amino acid sequence (SEQ ID NO: 2). The published genome sequence is derived from a haploid genome and is based on automated genome annotation. Therefore, the sequences of the cloned genes may differ from the published genome sequences. Differences may also have been introduced during PCR.

SEQ ID NO: 4 and SEQ ID NO: 6, respectively, differ by one amino acid from the amino acid sequence deduced from the genome. This difference is indicated in FIG. 1, where the two differing amino acids are shaded. The sequences of the other three cutinase-like proteins CC1G_03922, CC1G_11503, and CC1G_09365 are given in the Sequence Listing as SEQ ID NO: 7, SEQ ID NO: 8, and SEQ ID NO: 9, respectively.

The genes were transferred by LR recombination reactions from the pDONR221 vector to the *Trichoderma reesei* expression vector pMS186, giving rise to the plasmids pAWP26 (CC1G_09668.1), pAWP27 (CC1G_07482) and pAWP28 (CC1G_05430.1). The pMS186 vector contains the Gateway reading frame cassette C(RfC) inserted between the cbh1 (cellobiohydrolase 1) promoter and terminator, and a hygromycin resistance cassette. The LR recombination reaction was done with the Gateway Recombination kit (Invitrogen) as instructed by the manufacturer.

Example 6

Cloning of Novel Polyesterases from *Trichoderma reesei*

The cutinase (v1.2: tre17732, v2.0: tre60489, scaffold 7) and suberinase (v1.2: tre40871, v2.0: tre31227, scaffold 37) cDNA from *Trichoderma reesei* were isolated by RT-PCR from a cDNA expression library of *Trichoderma reesei* RutC-30 (Margolles-Clark E., et al., 1996) with primers which were designed to create a C-terminal $His_6$-tag and bearing phage lambda-based site specific recombination sequences; cutinase forward: (SEQ ID NO:20), cutinase reverse: (SEQ ID NO:21), suberinase forward: (SEQ ID NO:22, suberinase reverse: (SEQ ID NO:23). The native signal sequence of the cutinase was used, whereas the signal sequence of cbhI was used for the suberinase construct. The PCR reactions were done with the Phusion thermostable polymerase (Finnzymes, Finland) in a reaction mixture recommended by the manufacturer. The PCR program had an initial denaturation step of 30 seconds at 98° C., followed by 25 cycles of 10 seconds at 98° C., 30 seconds at 64° C. and 30 seconds at 72° C., where the annealing temperature was decreased with 1° C. per cycle until 50° C. was reached. This was followed by a final elongation step of 10 minutes at 72° C. The amplified PCR products were recombined into the Gateway donor vector pDONR221 (Invitrogen) by Gateway Recombination kit (Invitrogen) and sequenced. The sequences are shown in Table 3.

TABLE 3

Cloned *Trichoderma reesei* cutinase and suberinase sequences

| Gene | Cloned nucleotide sequence | Deduced amino acid sequence |
|---|---|---|
| T. reesei 17732 (cutinase) | SEQ ID NO: 10 | SEQ ID NO: 11 |
| T. reesei 40871 (suberinase) | SEQ ID NO: 12 | SEQ ID NO: 13 |

The cloned nucleotide sequence and deduced amino acid sequence of cutinase was longer at both 5' and 3' ends than predicted by the computational annotation of *T. reesei* genome.

The cutinase and suberinase genes were transferred by LR recombination reactions from the pDONR221 vector to the *Trichoderma reesei* expression vector pMS186, giving rise to the plasmids pAWP24 (cutinase) and pAWP25 (suberinase). The pMS186 vector contains the Gateway reading frame cassette C(RfC) inserted between the cbh1 (cellobiohydrolase 1) promoter and terminator, and a hygromycin resistance cassette. The LR recombination reaction was done with the Gateway Recombination kit (Invitrogen) as instructed by the manufacturer.

Example 7

Expression of Novel Polyesterases in *Trichoderma reesei*

The polyesterase genes were expressed in *T. reesei* under the strongly inducible promoter of the major cellulase gene cbh1. Circular expression vectors (5 μg) were transformed into the *T. reesei* cbh1 negative strain VTT-D-04966 by PEG-mediated transformation, essentially as described by Penttilä M., et al, 1987, and transformants were selected for hygromycin resistance on plates containing 125 μg/ml of hygromycin B. The transformants were streaked on the selective medium for two successive rounds and tested by PCR for integration into the genome. Positive transformants were purified by single-spore cultures and were tested for cutinase activity in liquid cultures using p-nitrophenylbutyrate (p-NPB) as a model substrate (Example 1). 50 ml of culture medium (TrMM+4% lactose, 2% spent grain, 100 mM PIPPS, pH 5.5) was inoculated with $1 \times 10^7$ spores and grown for a maximum of 10 days at 28° C. shaking at 250 rpm. All three *Trichoderma* constructs i.e. those trans-formed with *Coprinus* gene 09668, 07482, and 05430, respectively, showed p-NPB activity. The six transformants showing highest activities of each gene were re-cultivated for more thorough analysis. *C. cinereas* 09668 seemed to be most promising candidate and it was cultivated in a laboratory-scale fermenter. The most potential transformants (on the basis of the activity assay with p-NPB) carrying *T. reesei* cutinase or suberinase gene were also selected for cultivation in fermenter.

Example 8

Production of Novel Polyesterases in Laboratory-Scale Fermenter

The transformant of 09668 producing cutinase (CcCUT) was cultivated in a Braun Biostat C fermenter (B. Braun Biotech, Germany), working volume 20 liters. The medium contained (in g $l^{-1}$): lactose (60), $(NH_4)_2SO_4$ (5) and $KH_2PO_4$ (5). The liquid phase of the medium was an aqueous extract of distiller's spent grain prepared by heating 60 g $l^{-1}$ spent grain at 115° C. for 20 minutes in an autoclave, cooling and centrifuging to remove the solid components. The centrifugation supernatant containing both nitrogen source and inducers was used in the medium as the only liquid. Cultivation temperature was 28° C. and pH was 5.0-5.5 (controlled by addition of ammonium hydroxide and phosphoric acid). Dissolved oxygen was maintained at >30% by agitation at 300 . . . 700 rpm, with a constant aeration of 8 l $min^{-1}$. Foaming was controlled by automatic addition of Struktol J633 polyoleate antifoam agent (Schill & Seilacher, Germany). After the cultivation, cells were removed by centrifugation and the culture supernatant was concentrated by ultrafiltration using Millipore (France) BioMax 10 membranes, nominal cut-off 10 kDa.

The *C. cinereus* cutinase (CcCUT) was successfully produced in the fermenter. Cutinase production increased to a maximum of over 8000 nkat $ml^{-1}$ after 96 h (FIG. 2). A ten-fold culture filtrate had an esterase activity (with p-NPB) of 70 000 nkat $ml^{-1}$, a total protein content of 104 mg $ml^{-1}$, and an amount of cutinase of approx. 23 mg $ml^{-1}$. The presence of cutinolytic activity in the culture supernatant was also verified on isolated apple cutin before further studies (Table 4). Cutin was treated in the presence of 0.1% TRITON™ X-100 (non-ionic octylphenol ethoxylate surfactant) with culture supernatant (45 h sample, p-NPB-activity of 1780 nkat $ml^{-1}$) using enzyme dosages of 1000, 5000 and 20 000 nkat $g^{-1}$ substrate (pH 7, 40° C.).

TABLE 4

Cutinolytic activity of CcCUT

| Dosage (nkat/g) | Released fatty acids* (% of substrate) |
|---|---|
| Reference | 0.71 |
| 1 000 | 2.31 |
| 5 000 | 3.59 |
| 20 000 | 3.78 |

*total amount, containing mono- and oligomers

Figure 3:
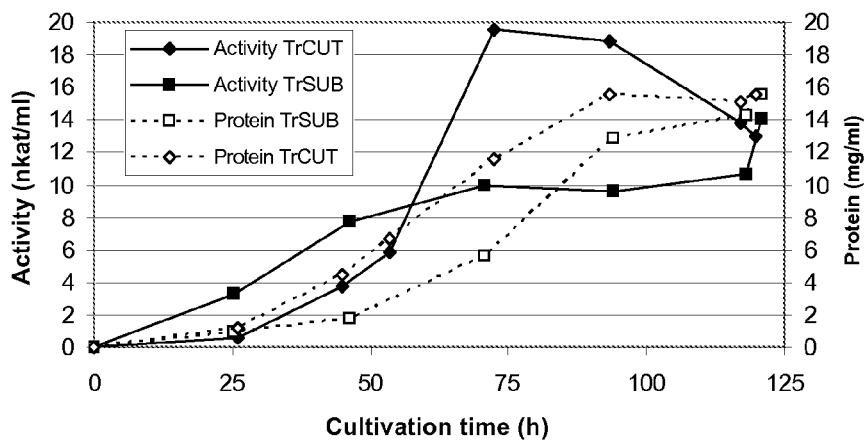
FIG. 3 shows extracellular production of *Trichoderma reesei* cutinase (TrCUT) and suberinase (TrSUB) in a 20 L bioreactor cultivation.

The transformants producing *Trichoderma reesei* cutinase (TrCUT) and suberinase (TrSUB) were cultivated in a laboratory fermenter similarly as described earlier for CcCUT. Enzyme activities are shown as a function of time in FIG. 3.

Example 9

Purification of Recombinant Enzymes

The presence of C-terminal His(6)-tag enabled a one-step purification of CcCUT and TrCUT using immobilized metal affinity chromatography (IMAC). The concentrated culture supernatant was applied to a chelating Sepharose FF column (Amersham Biosciences, Uppsala, Sweden) preloaded with $Ni^{2+}$ and equilibrated with 50 mM sodium phosphate containing 500 mM NaCl and 5 mM imidazole, pH 7.2. The column was washed with equilibrating buffer supplemented with 50 mM (for CcCUT) or 20 mM imidazole (for TrCUT) in order to remove the unbound material. The recombinant protein was eluted with equilibrating buffer supplemented with 200 mM imidazole and fractions were collected and screened for the activity on p-NPB and the presence of the protein by SDS-PAGE. SDS-PAGE (12% Tris-HCl Ready Gel, Bio-Rad) was performed according to Laemmli (1970), using Pre-stained SDS-PAGE Standards (Broad Range Cat. no. 161-0318, Bio-Rad or LMW, Cat. No 17-0446-01, GE Healthcare) and Coomassie Brilliant Blue (R350; Pharmacia) for staining the proteins.

The purified CcCUT showed homogeneity on SDS-PAGE and approx. 10 grams of purified enzyme was prepared for further characterization and hydrolysis studies. 3 grams of TrCUT was purified, the preparation having a purity around 95% (based on SDS-PAGE analysis). TrSUB is purified similar to CcCUT and TrCUT for characterization.

Example 10

Characterization of the Novel Polyesterases

The purified *Coprinus cinereus* (CcCUT) and *Trichoderma reesei* (TrCUT) cutinases were biochemically characterized with respect to size, activity, substrate specificity, pH and temperature characteristics.

Substrate Specificity

Figure 4:
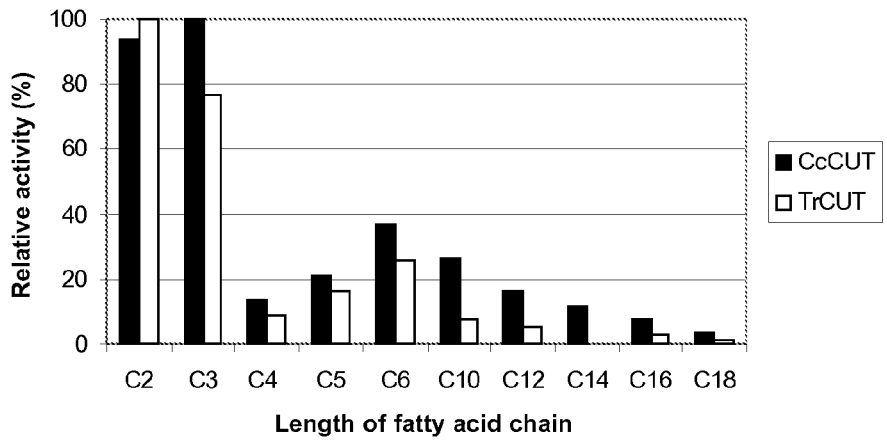
FIG. 4 shows the effects of fatty acid chain length on esterolytic activity of *Coprinus cinereus* cutinase 09668 (CcCUT) and *Trichoderma reesei* cutinase (TrCUT) measured at pH 7 and 40° C.

The substrate specificity was determined using p-nitrophenols esterified with acetate (C2), propionate (C3), butyrate (C4), valerate (C5), caproate (C6), caprate (C10), laurate (C12), myristate (C14), palmitate (C16) and stearate (C18). The concentrations of substrate dispersions were 5 mM. A lower concentration of p-nitrophenyl stearate (2.5 mM) was used due to its lower solubility. Activity assays were performed as described for p-nitrophenyl butyrate (p-NPB) at pH 7, 40° C. (Example 1). The specific activities obtained are shown in FIG. 4. CcCUT and TrCUT had higher activity on shorter (C2-C10) than on longer (C16 and C18) fatty acids. Surprisingly, the activities on p-NP acetate (C2) and propionate (C3) were observed to be clearly higher than on p-NPB (C4). The C4/C16 ratio of CcCUT and TrCUT was 1.8 and 3.1, respectively. Typically, cutinases have high activity on C2-C8 fatty acids and the ratio C4/C16 ratio is between 1-4. A C4/C16 ratio of about 1, or <1 indicates no cutinolytic activity (Kolattukudy, 1984).

Lipase and Cholesteryl Esterase Activity

Lipase activity was assayed using olive oil emulsion as substrate according to Kontkanen et al. (2004). The lipase activity of CcCUT and TrCUT is shown in Table 5.

The assay used for determination of cholesteryl esterase (CE) activity was based on the spectrophotometric determination of liberated cholesterol after hydrolysis of 4.3 mM cholesteryl oleate according to Tenkanen et al. (2002). CcCUT preparation showed no cholesteryl esterase activity. Activity in TrCUT preparation was not determined.

Protein Assay

Protein concentration was determined by the Bio-Rad DC protein assay kit (Bio-Rad, Richmond, Calif.) with bovine serum albumin as standard.

Temperature Stability

Temperature stability of CcCUT and TrCUT were investigated by incubating the enzymes at 30-80° C. for 1, 3 and 20 h at protein concentration of 5 mg/ml and pH 5 (20 mM sodium acetate buffer). After the incubations, the residual activity was measured using p-NPB as substrate (at pH 7 and 40° C.). CcCUT was rather stable at temperatures up to 50° C. but residual activity decreased sharply at 60° C. TrCUT was somewhat stable retaining 80% of its activity when incubated at 50° C. for 20 h or at 60° C. for 1 h (Table 5).

pH Stability

The pH stability of CcCUT and TrCUT was determined by incubating the purified enzyme solutions at different pH values at room temperature and at 50° C. for 20 h. The pH of the solution was adjusted with McIlvaine buffer (0.2 M $Na_2HPO_4$ and 0.1 M citric acid) at pH 2.2-8.0, 0.2 M Tris-HCl buffer at pH 7.2-9.1 or 0.2 M glycine-NaOH buffer at pH 8.6-10.6 to obtain protein concentration of 5 mg $ml^{-1}$. The residual activity was measured with p-NPB at pH 7 and 40° C. The results are shown in Table 5. It can be seen that both enzymes were active over a wide range of pH including the acidic range. The residual activity of CcCUT was about 80% at a pH of 3 at room temperature, whereas the residual activity at 50° C. was about 40% at pH 5, and about 100% at pH 6. TrCUT was shown to retain over 90% of it activity within the pH range of 4-7.

pH Optimum

Esterase activities of purified cutinase preparations were measured at different pH values using McIlvaine buffer (0.2 M $Na_2HPO_4$ and 0.1 M citric acid) at pH 2.3-8, 0.2 M Tris-HCl buffer at pH 7.2-9.1 and 0.2 M glycine-NaOH buffer at pH 8.6-10.6 using p-NPB as substrate. The reaction time was 10 minutes at 40° C. The results are shown in Table 5. The pH optimum of CcCUT was around 7-8, whereas TrCUT was shown to have two clearly different pH optima (around 4 and 8). Thus TrCUT is suitable for treatments in a more acidic range.

TABLE 5

Biochemical properties of *Coprinus cinereus* cutinase 09668 (CcCUT) and *Trichoderma reesei* cutinase (TrCUT).

| Property | | CcCUT | TrCUT |
|---|---|---|---|
| Molecular weight, kDa (SDS-PAGE) | | 22 (20.8[a]) | 28 (25.9[a]) |
| Length of mature protein (aa) | | 181 | 231 |
| Thermostability (pH 5) | T½ 50° C. | >20 h (70%) | >20 h (80%) |
| | T½ 55° C. | 3 h | n.d. |
| | T½ 60° C. | <1 h | 1.5 h |
| pH stability (20 h) | 50° C. | 6-9 | 4-7 |
| | 23° C. | 4-9 | n.d. |
| pH optimum (with p-NPB) | | 7-8 | 4 and 8 |
| Activity (nkat $mg^{-1}$) | Lipase | 234 | 88 |
| | CE | 0 | n.d. |

[a]theoretical Mw
n.d. not determined

Example 11

Hydrolysis of Isolated Apple Cutin

Isolated apple cutin was treated with CcCUT and TrCUT. The substrate was treated enzymatically and chemically in order to remove of carbohydrates and pectin as well as non-covalent lipids, respectively. Cutin was suspended in 0.2 M sodium-phosphate buffer, pH 8 in a concentration of 20 mg $ml^{-1}$ and treated with CcCUT and TrCUT at 45° C. for 20 h. The enzyme dosages were 1000 and 10 000 nkat $g^{-1}$ substrate (p-NPB-activity) and the treatments were performed with and without TRITON™ X-100 (non-ionic octylphenol ethoxylate surfactant) addition. The hydrolysates were extracted twice with 2 volumes of MTBE in order to recover all fatty acids, both mono- and oligomers, from the solid matrix. Free fatty acids in the MTBE extract were analysed directly and after alkali hydrolysis of released oligomers using the enzymatic colorimetric method (Free fatty acids, Roche Diagnostics Ltd). Amount of released fatty acids are shown in Table 6. Both cutinases were able to hydrolyse apple cutin.

TABLE 6

Treatment of apple cutin with CcCUT and TrCUT.

| | | No detergent | | 0.1% TRITON ™ X-100 (non-ionic octylphenol ethoxylate surfactant) | |
|---|---|---|---|---|---|
| Enzyme | Dosage (nkat/g) | Monomers* | Mono- and oligomers* | Monomers* | Mono-and oligomers* |
| Ref | 0 | 0.23 | 0.51 | 0.22 | 0.63 |
| CcCut | 1000 | 3.30 | 2.61 | 1.53 | 1.68 |
| | 10 000 | 7.30 | 10.08 | 3.97 | 6.50 |
| TrCut | 1000 | 0.85 | 1.21 | 0.57 | 0.74 |

*% of substrate, calculated as stearic acid (284.5 g/mol)

Example 12

Hydrolysis of Birch Bark Suberin

Steam exploded birch outer bark suberin was treated with CcCUT and TrCUT similarly as cutin treatments described above. The results are shown in Table 7.

TABLE 7

Treatment of birch bark suberin with CcCUT and TrCUT.

| | | No detergent | | 0.1% TRITON ™ X-100 (non-ionic octylphenol ethoxylate surfactant) | |
|---|---|---|---|---|---|
| Enzyme | Dosage (nkat/g) | Monomers* | Mono- and oligomers* | Monomers* | Mono-and oligomers* |
| Ref | 0 | 0.04 | 0.07 | 0.06 | 0.09 |
| CcCut | 1000 | 0.30 | 0.24 | 0.48 | 0.45 |
| | 10 000 | 1.91 | 1.75 | 2.70 | 2.67 |
| TrCut | 1000 | 0.31 | 0.33 | 0.41 | 0.40 |

*% of substrate, calculated as stearic acid (284.5 g/mol)

Example 13

Treatment of Peeled Wheat Grain

Peeled wheat grains were treated with cutinase (CcCUT) in order to enhance removal of testa which is mainly composed of unsubstituted linear xylan and cutin layers. Grains (2 g) were treated in water suspensions with a dry matter content of 20% at 30° C. for 2 h shaking (100 rpm). Enzyme dosages of 500 and 5000 nkat g−1 substrate (as p-NPB-activity) were tested for CcCUT. The effect of two different xylanases and a lipase were also studied. After enzyme treatments, centrifugation (9700 g/10 min) was applied to separate the liquid and solid phases. The grains were washed with water (10 ml), and centrifugation was repeated. The grains were freeze-dried and weighed in order to analyze weight loss. The reference treatments were performed under identical conditions but without enzyme additions. The amount of released fatty acids was analysed after MTBE extraction followed by dissolution of fatty acids into EtOH/TRITON™ (non-ionic octylphenol ethoxylate surfactant)/water solution. Reducing sugars were analyzed from liquid samples using DNSmethod (Bernfield, 1955).

The amounts of released fatty acids and solubilised carbohydrates after enzyme treatments are shown in Table 8. It can be seen that CcCUT increased clearly the amount of released fatty acids in used conditions. The treatments performed had no effect on the amount of carbohydrates. No changes on the visual appearance of the grains could be observed after the treatments indicating selective action on cutin.

TABLE 8

Enzymatic treatment of peeled wheat grains.

| Treatment | Dosage (nkat g−1) | Other enzymes | Fatty acids (mg) | Carbohydrates (mg) |
|---|---|---|---|---|
| Reference | — | — | 0.40 | 4.7 |
| CcCUT | — | xylanaseA 100 nkat g−1 | 0.32 | 5.3 |
| CcCUT | — | xylanaseB 100 nkat g−1 | 0.45 | 5.9 |
| CcCUT | 500 | — | 0.53 | 4.4 |
| CcCUT | 5000 | — | 1.23 | 3.7 |
| CcCUT | 500 | xylanaseA 100 nkat g−1 | 0.88 | 5.0 |
| CcCUT | 5000 | xylanaseA 100 nkat g−1 | 1.02 | 4.2 |
| CcCUT | 500 | xylanaseB 100 nkat g−1 | 1.08 | 4.9 |
| CcCUT | 5000 | xylanaseB 100 nkat g−1 | 0.98 | 4.8 |
| CcCUT | — | lipaseA 1000 nkat g−1 | 0.77 | 4.0 |
| CcCUT | 1000 | lipaseA 1000 nkat g−1 | 1.42 | 3.7 |

REFERENCES

Bernfeld, P. (1955) Amylases, a and b. In: Colowick, S. P. and Kaplan, N. O. (eds) Methods of enzymology, Vol 1, Academic press, NY, pp 149-158.

Carvalho, C. M. L., Aires-Barras, M. R., Cabral, J. M. S. (1999) Cutinase: from molecular level to bioprocess development. Biotechnol Bioeng. 66:17-34.

Coen, D. M. 2001. The polymerase chain reaction. In: Ausubel, F. M., Brent, R., Kingston, R. E., More, D. D., Seidman, J. G., Smith, K. and Struhl, K. (eds.) Current protocols in molecular biology. John Wiley & Sons. Inc., Hoboken, USA.

Davies, K. A., de Lorono, I., Foster, S. J., Li, D., Johnstone, K., Ashby, A. M. (2000) Evidence for a role of cutinase in pathogenicity of Pyrenopeziza brassicae on brassicas. Physiol. Mol. Plant. Pathol. 57:63-75.

Fett, W. F., Gerard, H. C., Moreau, R. A., Osman, S. F., Jones, L. E. (1992) Cutinase production by Streptomyces spp. Curr Microbiol. 25:165-71.

Garcia-Lepe, R., Nuero, O. M., Reyes, F. (1997) Lipases autolysed cultures of filamentous fungi, Letters in Applied Microbiology. 25(2):127-130

Gindro, K., Pezet, R. (1999) Purification and characterization of a 40.8-kDa cutinase in ungerminated conidia of Botrytis cinerea Pers.: Fr. FEMS Microbiol Letters 171:239-243.

Gellissen, G. (ed.) 2005. Production of recombinant proteins. Novel microbial and eukaryotic expression systems. Wiley-VCH Verlag Gmbh&Co. weinheim, Germany.

Kolattukudy, P. E. (1984) Cutinases from fungi and pollen. In: Lipases (Borgström, B., Brockman, T. Eds.). Elsevier, Amsterdam. 471-504.

Kontkanen, H., Tenkanen, M., Fagerström, R., Reinikainen, T. (2004) Characterisation of steryl esterase activities in commercial lipase preparations. J. Biotechnol. 108:51-59.

Köller, W., Allan, C. R., Kolattukudy, P. E. (1982) Role of cutinase and cell wall degrading enzymes in infection of Pisum sativum by Fusarium solani f. sp. pisi. Physiol Plant Pathol. 20:47-60.

Köller, W., Parker, D. M. (1989) Purification and characterization of cutinase from Venturia inaequalis. Phys Biochem. 79:278-83.

Maeda, H., Yamagata, Y., Abe, K., Hasegawa, F., Machida, M., Ishioka, R., Gomi, K., Nakajima, T. (2005) Purification and characterization of a biodegradable plastic-degrading enzyme from Aspergillus oryzae. Appl Microbiol Biotechnol. 67:778-88.

Margolles-Clark, E., Tenkanen, M., Nakari-Setälä, T., Penttilä, M. (1996) Cloning of genes encoding alpha-L-arabinofuranosidase and beta-xylosidase from Trichoderma reesei by expression in Saccharomyces cerevisiae. Appl Environ Microbiol. 62(10):3840-6.

Penttilä, M., Nevalainen, H., Rättö, M., Salminen, E., Knowles, J. K. C. (1987) A versatile transformation system for the cellulolytic filamentous fungus Trichoderma reesei, Gene 61:155-164

Raeder, U., Broda, P. (1985) Rapid preparation of DNA from filamentous fungi. Lett Appl Microbiol. 1:17-20.

Sambrook, J., Fritsch, E. F. and Maniatis, T. 1989. Molecular cloning: A laboratory manual, 2nd edn. Cold Spring Harbor Laboratory, Cold Spring Harbor N.Y.

Tenkanen, M., Kontkanen, H., Isoniemi, R., Spetz, P., Holmbom, B. (2002) Hydrolysis of steryl esters by a lipase (Lip 3) from Candida rugosa. Appl Microbiol Biotechnol. 60:120-127.

Thompson, J. D., Higgins D. G., Gibson T. J. (1994). CLUSTAL W: improving the sensitivity of progressive multiple sequence alignment through sequence weighting, position-specific gap penalties and weight matrix choice. Nucleic Acids Res. 22:4673-4680.

Trail, F., Köller, W. (1993) Diversity of cutinases from plant pathogenic fungi: Purification and characterization of two cutinases from Alternaria brassicola. Physiol Molec Plant Pathol. 42:205-20.

The invention claimed is:

1. An isolated polyesterase protein comprising an amino acid sequence having at least 90% sequence identity to the amino acid sequence of SEQ ID NO: 2, wherein the protein retains polyesterase activity.

2. The isolated polyesterase protein of claim 1, wherein said protein has at least 95% or 98% sequence identity to the amino acid sequence of SEQ ID NO: 2.

3. The isolated polyesterase protein of claim 1, wherein said protein has cutinase or suberinase activity, or both.

4. The isolated polyesterase protein of claim 3, which further has lipase activity.

5. The isolated polyesterase protein of claim 1, wherein said protein is obtained from *Coprinus cinereus*, and comprises the amino acid sequence of SEQ ID NO: 2, wherein the protein has cutinase or suberinase activity, or both.

6. An enzyme preparation comprising the protein of claim 1.

7. The isolated polyesterase protein of claim 1, wherein the protein comprises an amino acid sequence having at least 95% sequence identity to the amino acid sequence of SEQ ID NO: 2.

8. The isolated polyesterase protein of claim 1, wherein the protein comprises an amino acid sequence having at least 98% sequence identity to the amino acid sequence of SEQ ID NO: 2.

* * * * *

SEQUENCE LISTING

<160> NUMBER OF SEQ ID NOS: 23

<210> SEQ ID NO 1
<211> LENGTH: 714
<212> TYPE: DNA

-continued

<213> ORGANISM: Coprinus cinereus

<400> SEQUENCE: 1

```
atgaagttca ccactctcgc caccctcgcc ctcggcgccg tctccgctct cgctgcccca      60
gtcacagagc tcgagtcccg ccagctcttc tgcaggacg tgtacgtctt cttcgctcgt     120
ggaaccggtg aagtcggcac cttgggtacc gtcgttggtc ctggcctcag tgcagcggtc     180
aagctcgctg ttcgggactc tgtcgagttc gagggcattg actacccccgc cctcgtctcc     240
ggctacctcg ctggtggcga ccgtggtggt gcccgcacca tggcaaacaa ggtctcccaa     300
accgcgtccc gctgccccaa cgccaagatc ttcatctccg gctactcgta agttccgacg     360
ttccgtgact aaagctcagc gttccatggt gttgactcgc ctgtagacaa ggtgcccagg     420
tcacccacct cgctgctcgc cagctctccg ctgcagacca ggcgagagtc actggtgtcg     480
tcactttcgg tgacccatac agggatgatg ctctccccgg tggcctccaa agccgcagga     540
agacctactg caacgtcggt gacctcatct gtgccggcct tcctaccctc cttgctcccc     600
actttaccta tggatcggtg agtgctacct gccacaatag ctgactctcc tcgctgacct     660
gcattgaaac aggacacccc cgacgctgct cgatggatcg ccgctcgcgt ttag           714
```

<210> SEQ ID NO 2  
<211> LENGTH: 199  
<212> TYPE: PRT  
<213> ORGANISM: Coprinus cinereus

<400> SEQUENCE: 2

```
Met Lys Phe Thr Thr Leu Ala Thr Leu Ala Leu Gly Ala Val Ser Ala
1               5                   10                  15

Leu Ala Ala Pro Val Thr Glu Leu Glu Ser Arg Gln Leu Phe Cys Arg
            20                  25                  30

Asp Val Tyr Val Phe Phe Ala Arg Gly Thr Gly Glu Val Gly Thr Leu
        35                  40                  45

Gly Thr Val Val Gly Pro Gly Leu Ser Ala Ala Val Lys Leu Ala Val
    50                  55                  60

Arg Asp Ser Val Glu Phe Glu Gly Ile Asp Tyr Pro Ala Leu Val Ser
65                  70                  75                  80

Gly Tyr Leu Ala Gly Gly Asp Arg Gly Gly Ala Arg Thr Met Ala Asn
                85                  90                  95

Lys Val Ser Gln Thr Ala Ser Arg Cys Pro Asn Ala Lys Ile Phe Ile
            100                 105                 110

Ser Gly Tyr Ser Gln Gly Ala Gln Val Thr His Leu Ala Ala Arg Gln
        115                 120                 125

Leu Ser Ala Ala Asp Gln Ala Arg Val Thr Gly Val Val Thr Phe Gly
    130                 135                 140

Asp Pro Tyr Arg Asp Asp Ala Leu Pro Gly Gly Leu Gln Ser Arg Arg
145                 150                 155                 160

Lys Thr Tyr Cys Asn Val Gly Asp Leu Ile Cys Ala Gly Leu Pro Thr
                165                 170                 175

Leu Leu Ala Pro His Phe Thr Tyr Gly Ser Asp Thr Pro Asp Ala Ala
            180                 185                 190

Arg Trp Ile Ala Ala Arg Val
        195
```

<210> SEQ ID NO 3  
<211> LENGTH: 732  
<212> TYPE: DNA  
<213> ORGANISM: Coprinus cinereus

<400> SEQUENCE: 3

```
atgaagtttt ccgccctcgt cgccctcgcc ctcggcgctg ccaccacctt cgccgcccca    60
attggtctcg aagcgcgaca aggcacctgc agcgatgtct atgtcttttt cgtgcgaggg   120
acgactgaga ctcctgcacc cctaggcgac aggattgctc cgttttttcag ggatgcgctg   180
gtcaagctcg ttccagagaa atctgtggaa ttcactggcg tgccctatgc cgctgggttg   240
attggatatc tcatcggggg tgaccctgag ggtgccaaaa cgatggcgaa tatggttacg   300
acgactgtcc gccaatgttc gaatgcgaag attttcatgt ctgggtatag gtacgagttc   360
aaactacact tggttaaaac tggtgctcga tgattggtgc tcaatggttg tttcccgtct   420
tccagccaag gcgcccaggt gacccacctt gctgctcgtc aactttcaga tgaggatctc   480
gaccgcgtca ctggggtagt cacctttggc gacccgtaca aggacactgc ccttcccgga   540
acacttgagc agagacggaa gactttctgt cgtaatgggg atttgatttg cgaacgcgtg   600
catcttccgc ttcctcctca tttcgaatat cataacgtac gtccttcatc gtattgatta   660
taggtcctgt cggctaatgg gtacatctag gatgccgaag aggctgctcg ctgggtcgct   720
gaccgcgttt ag                                                       732
```

<210> SEQ ID NO 4
<211> LENGTH: 200
<212> TYPE: PRT
<213> ORGANISM: Coprinus cinereus

<400> SEQUENCE: 4

```
Met Lys Phe Ser Ala Leu Val Ala Leu Ala Leu Gly Ala Ala Thr Thr
1               5                   10                  15

Phe Ala Ala Pro Ile Gly Leu Glu Ala Arg Gln Gly Thr Cys Ser Asp
            20                  25                  30

Val Tyr Val Phe Phe Val Arg Gly Thr Thr Glu Thr Pro Ala Pro Leu
        35                  40                  45

Gly Asp Arg Ile Ala Pro Phe Phe Arg Asp Ala Leu Val Lys Leu Val
    50                  55                  60

Pro Glu Lys Ser Val Glu Phe Thr Gly Val Pro Tyr Ala Ala Gly Leu
65                  70                  75                  80

Ile Gly Tyr Leu Ile Gly Gly Asp Pro Glu Gly Ala Lys Thr Met Ala
                85                  90                  95

Asn Met Val Thr Thr Thr Val Arg Gln Cys Ser Asn Ala Lys Ile Phe
            100                 105                 110

Met Ser Gly Tyr Ser Gln Gly Ala Gln Val Thr His Leu Ala Ala Arg
        115                 120                 125

Gln Leu Ser Asp Glu Asp Leu Asp Arg Val Thr Gly Val Val Thr Phe
    130                 135                 140

Gly Asp Pro Tyr Lys Asp Thr Ala Leu Pro Gly Thr Leu Glu Gln Arg
145                 150                 155                 160

Arg Lys Thr Phe Cys Arg Asn Gly Asp Leu Ile Cys Glu Arg Val His
                165                 170                 175

Leu Pro Leu Pro Pro His Phe Glu Tyr His Asn Asp Ala Glu Glu Ala
            180                 185                 190

Ala Arg Trp Val Ala Asp Arg Val
        195                 200
```

<210> SEQ ID NO 5
<211> LENGTH: 823
<212> TYPE: DNA

<213> ORGANISM: Coprinus cinereus

<400> SEQUENCE: 5

```
atggtctcca aatcactcac ctccctcgtc ctcctcgcct tcaccctcac cggtgtcgca      60
gcggccccccg cccccaccac ccctgcgcc caagtgcaca tcatcgccgc cgcgcatcg      120
actgagcccc cgggccccgg catcgtcggt caactcatca cccagatcca gaaccagagt    180
tctcaaaccg tttccaccga ctcggtcgat taccctgcta cgcttgagaa ctacaacgag    240
agctcgtcgg cgggtactgc ggccctcaag acgcacttga caaaccaggc gaataggtgc    300
cctaatcaga agattgtgct tattgggtac tcgcaggtga ggatggattg ctagtactac    360
tagtgcatcg ggctaagttg ttgatgggct tgcgttttcg tatagggcgc tcatatcatc    420
ggtgacactc tcgccggtgg aggaggcggg ctcttgggca cccgaactcc cgctatcgac    480
tctagcatcg ccaaccgagg ttcgtctccc ttcctctttc ttccaccccc cacccccact    540
caagggcctc tctccccccaa cagtcgtcgc cgtagccaaa tcggcgacc cccgccacgt    600
ctccggcaag tcctacaacg agggcacagc tcgcagggac ggcatgttcc cccgcggcct    660
gacccaggac tacagcctca ccttccgctc cgcgtcaag agctggtgcg acttcaacga    720
tttgttctgt gcttcgggtc tttcgactat cgtccatttg acgtaccttg agaggtacca    780
gaacgatgct gcgaggtttg ttcttgataa gattggtggt taa                      823
```

<210> SEQ ID NO 6
<211> LENGTH: 229
<212> TYPE: PRT
<213> ORGANISM: Coprinus cinereus

<400> SEQUENCE: 6

```
Met Val Ser Lys Ser Leu Thr Ser Leu Val Leu Leu Ala Phe Thr Leu
  1               5                  10                  15

Thr Gly Val Ala Ala Ala Pro Ala Pro Thr Thr Pro Cys Ala Gln Val
             20                  25                  30

His Ile Ile Ala Ala Arg Ala Ser Thr Glu Pro Pro Gly Pro Gly Ile
         35                  40                  45

Val Gly Gln Leu Ile Thr Gln Ile Gln Asn Gln Ser Ser Gln Thr Val
     50                  55                  60

Ser Thr Asp Ser Val Asp Tyr Pro Ala Thr Leu Glu Asn Tyr Asn Glu
 65                  70                  75                  80

Ser Ser Ser Ala Gly Thr Ala Ala Leu Lys Thr His Leu Thr Asn Gln
                 85                  90                  95

Ala Asn Arg Cys Pro Asn Gln Lys Ile Val Leu Ile Gly Tyr Ser Gln
            100                 105                 110

Gly Ala His Ile Ile Gly Asp Thr Leu Ala Gly Gly Gly Gly Leu
        115                 120                 125

Leu Gly Thr Arg Thr Pro Ala Ile Asp Ser Ser Ile Ala Asn Arg Val
130                 135                 140

Val Ala Val Ala Lys Phe Gly Asp Pro Arg His Val Ser Gly Lys Ser
145                 150                 155                 160

Tyr Asn Glu Gly Thr Ala Arg Arg Asp Gly Met Phe Pro Arg Gly Leu
                165                 170                 175

Thr Gln Asp Tyr Ser Leu Thr Phe Arg Ser Arg Val Lys Ser Trp Cys
            180                 185                 190

Asp Phe Asn Asp Leu Phe Cys Ala Ser Gly Leu Ser Thr Ile Val His
        195                 200                 205

Leu Thr Tyr Leu Glu Arg Tyr Gln Asn Asp Ala Ala Arg Phe Val Leu
```

```
                   210                 215                 220
Asp Lys Ile Gly Gly
225

<210> SEQ ID NO 7
<211> LENGTH: 199
<212> TYPE: PRT
<213> ORGANISM: Coprinus cinereus

<400> SEQUENCE: 7

Met Lys Phe Thr Thr Leu Val Thr Leu Ala Leu Gly Ala Val Ser Ala
1               5                   10                  15

Leu Ala Ala Pro Ala Ala Glu Leu Glu Ser Arg Gln Leu Phe Cys Arg
            20                  25                  30

Asp Val Tyr Val Phe Phe Ala Arg Gly Thr Gly Glu Ile Gly Thr Leu
        35                  40                  45

Gly Thr Val Val Gly Pro Ser Phe Ser Ala Ala Val Ser Leu Ala Val
    50                  55                  60

Arg Gly Ser Val Asp Phe Glu Gly Ile Asp Tyr Pro Ala Leu Val Thr
65                  70                  75                  80

Gly Tyr Leu Ala Gly Asp Arg Gly Ala Arg Thr Met Ala Asp
                85                  90                  95

Lys Val Ala Ser Thr Ala Ser Arg Cys Pro Asn Ala Lys Ile Phe Ile
            100                 105                 110

Ser Gly Tyr Ser Gln Gly Ala Gln Val Thr His Leu Ala Ala Arg Gln
        115                 120                 125

Leu Ser Ala Ala Asn Gln Ala Arg Val Thr Gly Val Thr Phe Gly
    130                 135                 140

Asp Pro Tyr Arg Asp Ala Leu Pro Gly Leu Asp Ser Arg Arg
145                 150                 155                 160

Lys Thr Tyr Cys Asn Phe Gly Asp Leu Ile Cys Asp Gly Leu Pro Thr
                165                 170                 175

Ile Leu Ala Pro His Leu Thr Tyr Gly Ser Asp Ala Ser Asp Ala Ala
            180                 185                 190

Arg Trp Val Ala Ala Arg Val
        195

<210> SEQ ID NO 8
<211> LENGTH: 199
<212> TYPE: PRT
<213> ORGANISM: Coprinus cinereus

<400> SEQUENCE: 8

Met Lys Phe Phe Ala Leu Ala Thr Leu Ala Ile Gly Ala Leu Ser Ala
1               5                   10                  15

Leu Ala Ala Pro Val Ala Gln Ile Asp Thr Arg Gln Leu Arg Cys Asp
            20                  25                  30

Asp Val Tyr Val Phe Phe Ala Arg Gly Thr Thr Glu Ile Gly Thr Leu
        35                  40                  45

Gly Thr Val Ile Gly Pro Arg Leu Arg Thr Ala Val Ser Arg Ala Val
    50                  55                  60

Arg Gly Ser Val Thr Phe Glu Gly Ile Asp Tyr Pro Ala Val Val Ala
65                  70                  75                  80

Gly Phe Leu Ala Gly Asp Arg Gly Ala Arg Thr Met Ala Gln
                85                  90                  95

Lys Val Ser Ser Ile Ala Ala Gln Cys Pro Asp Ala Lys Ile Phe Ile
            100                 105                 110
```

```
Ser Gly Tyr Ser Gln Gly Ala Gln Val Thr His Leu Ala Ala Arg Gln
        115                 120                 125

Leu Ser Ala Ala Asp Gln Ala Arg Val Thr Gly Val Ile Thr Phe Gly
    130                 135                 140

Asp Pro Asn Arg Asp Arg Ala Leu Pro Gly Gly Leu Glu Asn Arg Arg
145                 150                 155                 160

Lys Thr Phe Cys Asn Ala Gly Asp Leu Ile Cys Ala Gly Arg Ser Thr
                165                 170                 175

Ile Leu Leu Pro His Leu Thr Tyr Gly Ser Asp Ala Thr Glu Ala Ala
            180                 185                 190

Ser Phe Ile Ala Gly Arg Val
        195

<210> SEQ ID NO 9
<211> LENGTH: 216
<212> TYPE: PRT
<213> ORGANISM: Coprinus cinereus

<400> SEQUENCE: 9

Met Arg Leu Ser Pro Leu Leu Pro Leu Ile Thr Leu Ala Ser Leu Thr
1               5                   10                  15

Leu Ala Thr Pro Val Pro Ile Pro Asn Pro Ile Ile Glu His Asp Asp
            20                  25                  30

Leu Asp Ile Arg Asp Leu Leu Glu Ala Arg Gln Val Thr Cys Arg Ser
        35                  40                  45

Val His Val Leu Phe Ala Arg Gly Thr Ala Glu Thr Pro Thr Leu Gly
    50                  55                  60

Glu Val Val Gly Pro Gly Phe Arg Asp Asn Leu Ile Lys Val Leu Pro
65                  70                  75                  80

Ser Ser Arg Thr Leu Ser Phe Ala Gly Ile Ser Tyr Ala Ala Ser Tyr
                85                  90                  95

Leu Gly Tyr Leu Gln Gly Gly Asp Lys Glu Gly Ala Lys Thr Met Ala
            100                 105                 110

Thr Ala Ala Ala Asn Ile Ala Lys Ser Cys Pro Ser Ala Lys Ile Phe
        115                 120                 125

Leu Ser Gly Tyr Ser Gln Gly Ala Gln Val Val His Leu Ala Ala Ala
    130                 135                 140

Gln Leu Ala Ser Ser Val Gln Ser Arg Ile Asn Gly Val Ile Thr Phe
145                 150                 155                 160

Gly Asp Pro Tyr Val Lys Arg Ala Leu Pro Gly Ala Met Glu Asn Arg
                165                 170                 175

Arg Lys Thr Phe Cys Asn Asp Gly Asp Lys Ile Cys Glu Gly Leu Pro
            180                 185                 190

Leu Val Thr Asp Pro His Met Asn Tyr Lys Ser Ser Trp Asp Pro Ala
        195                 200                 205

Ala Arg Trp Val Ala Phe Arg Val
    210                 215

<210> SEQ ID NO 10
<211> LENGTH: 1120
<212> TYPE: DNA
<213> ORGANISM: Trichoderma reesei

<400> SEQUENCE: 10
caggacaggt gaggagtata taaagagtct ggattgactc cgagttctac ttcctctcgg      60
ccattctctg gtgtctcttg gagcaaaagc agcccttcag cctctcagca tcttcactcg     120
```

-continued

```
caaaaaaacc cacttacaag atgcggtcct tggccattct caccaccctc ctcgcaggcc    180
atgcctttgc ataccccaag ccagcccccc agtcagtcaa tcgcagggac tggccttcga    240
tcaacgagtt cctctctgag ttggccaagg tgatgcccat tggcgacacc atcacggctg    300
cctgcgacct cattagcgat ggtgaagacg ccgctgcttc cctctttggc atctcggaga    360
cggaaaacga tccttgcggc gacgtgacag tcttgtttgc tcgaggcact tgcgatcctg    420
gaaacgtcgg cgtgcttgtc ggcccttggt tctttgattc tctgcagacg gcgcttggta    480
gcaggacctt gggcgtcaag ggagttccgt atcctgcgag cgtgcaggac ttcctgtcgg    540
gctccgttca gaatggcatc aacatgtaag tctctcccat catgacggta cttatccatt    600
acaatgtcaa ccaagccaga tactgactct tgatgtttaa aaaagggcca accagatcaa    660
gtctgtcctc cagagctgcc ccaacaccaa gctcgtcctc ggcggctact cccagggaag    720
catggtcgtc cacaacgcgg cgagcaacct cgacgccgcg acaatgtcaa agatcagcgc    780
cgtggtgctc tttggcgacc cttactacgg caagcccgtg gctaactttg acgcggctaa    840
gacgctggtt gtgtgccatg atggagacaa catttgccag ggtggtgaca ttatcttgtt    900
gccgcatttg acgtatgccg aagatgcgga tacggctgct gcttttgtgg tgcctcttgt    960
ttcttgaagt cttggagagg gttacggaag aggttgtgag agtcaaagta tggagaatgg   1020
gcgaacataa aaaaaaggga tcaatgattg tatatagcga aagccactga acatattgta   1080
tataagcaag cgttatgaga tacatcaatc atgttttgac                         1120
```

<210> SEQ ID NO 11
<211> LENGTH: 248
<212> TYPE: PRT
<213> ORGANISM: Trichoderma reesei

<400> SEQUENCE: 11

Met Arg Ser Leu Ala Ile Leu Thr Thr Leu Leu Ala Gly His Ala Phe
1               5                   10                  15

Ala Tyr Pro Lys Pro Ala Pro Gln Ser Val Asn Arg Arg Asp Trp Pro
                20                  25                  30

Ser Ile Asn Glu Phe Leu Ser Glu Leu Ala Lys Val Met Pro Ile Gly
            35                  40                  45

Asp Thr Ile Thr Ala Ala Cys Asp Leu Ile Ser Asp Gly Glu Asp Ala
        50                  55                  60

Ala Ala Ser Leu Phe Gly Ile Ser Glu Thr Glu Asn Asp Pro Cys Gly
65                  70                  75                  80

Asp Val Thr Val Leu Phe Ala Arg Gly Thr Cys Asp Pro Gly Asn Val
                85                  90                  95

Gly Val Leu Val Gly Pro Trp Phe Phe Asp Ser Leu Gln Thr Ala Leu
            100                 105                 110

Gly Ser Arg Thr Leu Gly Val Lys Gly Val Pro Tyr Pro Ala Ser Val
        115                 120                 125

Gln Asp Phe Leu Ser Gly Ser Val Gln Asn Gly Ile Asn Met Ala Asn
    130                 135                 140

Gln Ile Lys Ser Val Leu Gln Ser Cys Pro Asn Thr Lys Leu Val Leu
145                 150                 155                 160

Gly Gly Tyr Ser Gln Gly Ser Met Val Val His Asn Ala Ala Ser Asn
                165                 170                 175

Leu Asp Ala Ala Thr Met Ser Lys Ile Ser Ala Val Val Leu Phe Gly
            180                 185                 190

Asp Pro Tyr Tyr Gly Lys Pro Val Ala Asn Phe Asp Ala Ala Lys Thr

```
                 195                 200                 205
Leu Val Val Cys His Asp Gly Asp Asn Ile Cys Gln Gly Gly Asp Ile
        210                 215                 220

Ile Leu Leu Pro His Leu Thr Tyr Ala Glu Asp Ala Asp Thr Ala Ala
225                 230                 235                 240

Ala Phe Val Val Pro Leu Val Ser
                245

<210> SEQ ID NO 12
<211> LENGTH: 1332
<212> TYPE: DNA
<213> ORGANISM: Trichoderma reesei

<400> SEQUENCE: 12
atgacgtgga atccagatat tgcgacctgg ttgctgctgt tggcgctggc tccaatccgc      60
ggtctctgcc tggttgcgca gggccgtgga tggcagccgt acgagcatcg ccctgaaaat     120
gaacagctgg tgctacaacc tcctcctcca gactcgtccg cagccactcg accctccgct     180
ccctacgcac cgcccttccc cagtcgacca ggcagccgtc cgtccggctt tattgccctc     240
ggcgactcgt actcggccgg cataggcaca ggcctcatca atggaccgaa agatgaatgt     300
cgccgcggtg ccaacgccta cccggtgctg gtgcagcgcg acctccaccg cagtctggac     360
gggggccacg acccaacctt tcagtttctc tcctgcacgg gctctactgt tggtgacatg     420
cttaccgggg ccgagcgcag ccagatcgat ggcttcaaca caacctcgac ggccgacttt     480
gctcttctct ccattggcgg caacgacctg gcttcttcg acatcatgaa tagctgcatc     540
ttccgattct acagcttcta ctccggcacc tgcgagactg ctctccgcca cgccgacgag     600
cagatggcca gttcggattt tgaaaaccgt cttcgacttg tcatcatgga gattctcgac     660
cgcgtccgct gggagaagag gccgtggttc accattaccg tgacgggata tgcgcgcttc     720
ttcaacgcgg atacggacga gtgcgacgac tactcctttg gcatgtggtg gcgcggcccc     780
aagctggagc gcaagcttcg ccagcgcatg aacgacatgg ttgtcgacgt caacaacaag     840
atccggcgtt cagtcgacgc catcaacgcc gcctttgccg agccccgggt cctctttgtc     900
gactacgacg aggcctttga ggggcatcgc ttctgcgagc aggcgtcgt tgagcccgac     960 tacgcgagaa acgagacctg gttcttcctt gtcggcggcc tggacaacaa cccgagcgcg    1020
gagaagtcgg tgctcgtggc agaagatgcc ctgttgcctc ccgactctcc actaatcgac    1080
ccggagaact gcctcgaccc ggcacagacg tccggggact ggggggagct ggccttgtgt    1140
atgatggcca tggccgctga gagggacccc atgcttcgaa aggcagacgg gcgggttgtg    1200
gcggagaatt cgatgtggta tgtgcctaca tattacggca agacgtttca tccgcggagt    1260
cttggccaca tggcaatgag agatcggatc tacaaggcat ggcgtgaaat gcacgttccg    1320
acgatgagct ga                                                       1332

<210> SEQ ID NO 13
<211> LENGTH: 443
<212> TYPE: PRT
<213> ORGANISM: Trichoderma reesei

<400> SEQUENCE: 13

Met Thr Trp Asn Pro Asp Ile Ala Thr Trp Leu Leu Leu Ala Leu
1               5                   10                  15

Ala Pro Ile Arg Gly Leu Cys Leu Val Ala Gln Gly Arg Gly Trp Gln
            20                  25                  30

Pro Tyr Glu His Arg Pro Glu Asn Glu Gln Leu Val Leu Gln Pro Pro
```

```
                35                  40                  45
Pro Pro Asp Ser Ser Ala Ala Thr Arg Pro Ser Ala Pro Tyr Ala Pro
             50                  55                  60
Pro Phe Pro Ser Arg Pro Gly Ser Arg Pro Ser Gly Phe Ile Ala Leu
 65                  70                  75                  80
Gly Asp Ser Tyr Ser Ala Gly Ile Gly Thr Gly Leu Ile Asn Gly Thr
                 85                  90                  95
Glu Asp Glu Cys Arg Arg Gly Ala Asn Ala Tyr Pro Val Leu Val Gln
                100                 105                 110
Arg Asp Leu His Arg Ser Leu Asp Gly Gly His Asp Pro Thr Phe Gln
                115                 120                 125
Phe Leu Ser Cys Thr Gly Ser Thr Val Gly Asp Met Leu Thr Gly Ala
            130                 135                 140
Glu Arg Ser Gln Ile Asp Gly Phe Asn Thr Thr Ser Thr Ala Asp Phe
145                 150                 155                 160
Ala Leu Leu Ser Ile Gly Gly Asn Asp Leu Gly Phe Phe Asp Ile Met
                165                 170                 175
Asn Ser Cys Ile Phe Arg Phe Tyr Ser Phe Tyr Ser Gly Thr Cys Glu
            180                 185                 190
Thr Ala Leu Arg His Ala Asp Glu Gln Met Ala Ser Ser Asp Phe Glu
            195                 200                 205
Asn Arg Leu Arg Leu Val Ile Met Glu Ile Leu Asp Arg Val Arg Trp
            210                 215                 220
Glu Lys Arg Pro Trp Phe Thr Ile Thr Val Thr Gly Tyr Ala Arg Phe
225                 230                 235                 240
Phe Asn Ala Asp Thr Asp Glu Cys Asp Asp Tyr Ser Phe Gly Met Trp
                245                 250                 255
Trp Arg Gly Pro Lys Leu Glu Arg Lys Leu Arg Gln Arg Met Asn Asp
            260                 265                 270
Met Val Asp Val Asn Asn Lys Ile Arg Arg Ser Val Asp Ala Ile
            275                 280                 285
Asn Ala Ala Phe Ala Glu Pro Arg Val Leu Phe Val Asp Tyr Asp Glu
290                 295                 300
Ala Phe Glu Gly His Arg Phe Cys Glu Pro Gly Val Val Glu Pro Asp
305                 310                 315                 320
Tyr Ala Arg Asn Glu Thr Trp Phe Phe Leu Val Gly Gly Leu Asp Asn
                325                 330                 335
Asn Pro Ser Ala Glu Lys Ser Val Leu Val Ala Glu Asp Ala Leu Leu
            340                 345                 350
Pro Pro Asp Ser Pro Leu Ile Asp Pro Glu Asn Cys Leu Asp Pro Ala
            355                 360                 365
Gln Thr Ser Gly Asp Trp Gly Glu Leu Ala Leu Cys Met Met Ala Met
            370                 375                 380
Ala Ala Glu Arg Asp Pro Met Leu Arg Lys Ala Asp Gly Arg Val Val
385                 390                 395                 400
Ala Glu Asn Ser Met Trp Tyr Val Pro Thr Tyr Tyr Gly Lys Thr Phe
                405                 410                 415
His Pro Arg Ser Leu Gly His Met Ala Met Arg Asp Arg Ile Tyr Lys
                420                 425                 430
Ala Trp Arg Glu Met His Val Pro Thr Met Ser
            435                 440

<210> SEQ ID NO 14
<211> LENGTH: 52
```

```
<212> TYPE: DNA
<213> ORGANISM: Artificial
<220> FEATURE:
<223> OTHER INFORMATION: 09668 forward primer

<400> SEQUENCE: 14
ggggacaagt ttgtacaaaa aagcaggctt catgaagttc accactctcg cc          52

<210> SEQ ID NO 15
<211> LENGTH: 71
<212> TYPE: DNA
<213> ORGANISM: Artificial
<220> FEATURE:
<223> OTHER INFORMATION: 09668 reverse primer

<400> SEQUENCE: 15
ggggaccact ttgtacaaga aagctgggtc ctagtggtgg tggtggtggt gaacgcgagc   60
ggcgatccat c                                                        71

<210> SEQ ID NO 16
<211> LENGTH: 52
<212> TYPE: DNA
<213> ORGANISM: Artificial
<220> FEATURE:
<223> OTHER INFORMATION: 07482 forward primer

<400> SEQUENCE: 16
ggggacaagt ttgtacaaaa aagcaggctt catgaagttt ccgccctcg tc            52

<210> SEQ ID NO 17
<211> LENGTH: 70
<212> TYPE: DNA
<213> ORGANISM: Artificial
<220> FEATURE:
<223> OTHER INFORMATION: 07482 reverse primer

<400> SEQUENCE: 17
ggggaccact ttgtacaaga aagctgggtc ctagtggtgg tggtggtggt gaacgcggtc   60
agcgacccag                                                          70

<210> SEQ ID NO 18
<211> LENGTH: 53
<212> TYPE: DNA
<213> ORGANISM: Artificial
<220> FEATURE:
<223> OTHER INFORMATION: 05430 forward primer

<400> SEQUENCE: 18
ggggacaagt ttgtacaaaa aagcaggctt catggtctcc aaatcactca cct          53

<210> SEQ ID NO 19
<211> LENGTH: 75
<212> TYPE: DNA
<213> ORGANISM: Artificial
<220> FEATURE:
<223> OTHER INFORMATION: 05430 reverse primer

<400> SEQUENCE: 19
ggggaccact ttgtacaaga aagctgggtc ctagtggtgg tggtggtggt gaccaccaat   60
cttatcaaga acaaa                                                    75

<210> SEQ ID NO 20
<211> LENGTH: 52
<212> TYPE: DNA
<213> ORGANISM: Artificial
```

```
<220> FEATURE:
<223> OTHER INFORMATION: 17732 forward primer

<400> SEQUENCE: 20
ggggacaagt tgtacaaaa aagcaggctt catgcggtcc ttggccattc tc            52

<210> SEQ ID NO 21
<211> LENGTH: 74
<212> TYPE: DNA
<213> ORGANISM: Artificial
<220> FEATURE:
<223> OTHER INFORMATION: 17732 reverse primer

<400> SEQUENCE: 21
ggggaccact ttgtacaaga aagctgggtc ctagtggtgg tggtggtggt gagaaacaag   60
aggcaccaca aaag                                                    74

<210> SEQ ID NO 22
<211> LENGTH: 101
<212> TYPE: DNA
<213> ORGANISM: Trichoderma reesei

<400> SEQUENCE: 22
ggggacaagt tgtacaaaa aagcaggctt catgtatcgg aagttggccg tcatctcggc    60
cttcttggcc acagctcgtg ctctctgcct ggttgcgcag g                      101

<210> SEQ ID NO 23
<211> LENGTH: 72
<212> TYPE: DNA
<213> ORGANISM: Trichoderma reesei

<400> SEQUENCE: 23
ggggaccact ttgtacaaga aagctgggtc ctagtggtgg tggtggtggt gttgccatgt   60
ggccaagact cc                                                      72
```